United States Patent [19]

Nishiyama et al.

[11] 4,380,670
[45] Apr. 19, 1983

[54] PROCESS FOR PRODUCING 1,3,5-TRIAMINOBENZENE

[75] Inventors: Ryuzo Nishiyama, Takatsuki; Kanichi Fujikawa, Moriyama; Isao Yokomichi, Moriyama; Itaru Shigehara, Moriyama; Mikio Miyaji, Shiga, all of Japan

[73] Assignee: Ishihara Sangyo Kaisha Ltd., Osaka, Japan

[21] Appl. No.: 250,552

[22] Filed: Apr. 3, 1981

[51] Int. Cl.$^3$ .............................................. C07C 85/04
[52] U.S. Cl. .................................. 564/407; 564/305; 564/442
[58] Field of Search ......................................... 564/407

[56] References Cited

FOREIGN PATENT DOCUMENTS

| 204848 | 12/1907 | Fed. Rep. of Germany | 564/407 |
|---|---|---|---|
| 2436111 | 6/1975 | Fed. Rep. of Germany | 564/407 |
| 50-100028 | 8/1975 | Japan | 564/407 |
| 51-68530 | 6/1976 | Japan | 564/407 |
| 51-95026 | 8/1976 | Japan | 564/407 |
| 53-63323 | of 1978 | Japan . | |
| 440697 | 1/1936 | United Kingdom | 564/407 |

*Primary Examiner*—John Doll
*Attorney, Agent, or Firm*—Oblon, Fisher, Spivak, McClelland & Maier

[57] ABSTRACT

An aminobenzene is produced by reacting a chlorobenzene with ammonia in the presence of a copper type catalyst, namely by reacting ammonia with 3,5-diaminochlorobenzene to produce 1,3,5-triaminobenzene at a temperature of 150° to 250° C. at a molar ratio of ammonia of 2 to 10 to 3,5-diaminochlorobenzene in the presence of a copper compound catalyst.

7 Claims, No Drawings

PROCESS FOR PRODUCING 1,3,5-TRIAMINOBENZENE

BACKGROUND OF THE INVENTION

1. Field of the Invention:

The present invention relates to a process for producing 1,3,5-triaminobenzene by reacting ammonia with 3,5-diaminochlorobenzene in the presence of a copper compound catalyst.

2. Description of the Prior Art:

1,3,5-Triaminobenzene which has amino radicals at 1,3 and 5-positions on benzene nuclear is an important source in industrial organic syntheses. It has been difficult to produce 1,3,5-triaminobenzene in an industrial process. It has been known to produce 1,3,5-triaminobenzene by the following processes.

(1) The process for reducing 1,3,5-trinitrobenzene obtained by using 2,4,6-trinitrotoluene as a source (Chemical Abstract Vol. 62, 9047 e(1965)).

(2) The process for reducing 2,4,6-trinitrochlorobenzene obtained by using 2,4,6-trinitrophenol as a source (Yuki Kagobutsu Gosei Ho Vol. 9 page 87-88 edited by Yuki Gosei Kagaku Kyokai). These processes are disadvantageous as an industrial process because explosive nitrobenzenes are used or complicated reaction steps are needed.

On the other hand, the process for producing 3,5-dichloroaniline or 3,5-diaminochhlorobenzene by an amination of 1,3,5-trichlorobenzene has been disclosed (Yuki Gosei Kagaku Vol. 36 No. 9 (1978) page 784-788). The process for producing 3,5-dichloroaniline by an amination of 1-bromo-3,5-dichhlorobenzene has been disclosed (Japanese Unexamined Patent Publication No. 633 23/1978). In these references, there is not any disclosure of a production of 1,3,5-triaminobenzene.

If it is possible to produce directly 1,3,5-triaminobenzene by an amination of sym-trihalogenobenzene, the disadvantages of the conventional processes can be overcome. This is remarkably advantageous however, such desired reaction is not performed. This fact is confirmed by the description of Yuki Gosei Kagaku that in the amination of 1,3,5-trichlorobenzene in the presence of a copper type catalyst, 3,5-dichloroaniline is produced at a ratio of 30 to 40% and also m-dichlorobenzene as a by-product is produced at a ratio of 60 to 70% by a dechlorination.

SUMMARY OF THE INVENTION

It is an object of the present invention to provide a process for producing 1,3,5-triaminobenzene without using any explosive compound or a complicated reaction process.

It is another object of the present invention to provide a process for producing 1,3,5-triaminobenzene under a mild reaction condition with less side reaction in a simple reaction step which is advantageous in an industrial process.

It is the other object of the present invention to provide a process for producing 1,3,5-triaminobenzene at a high yield by using economically easily available starting material and catalyst.

The other objects of the present invention will be apparent from the following description.

The foregoing objects of the present invention have been attained by producing 1,3,5-triaminobenzene by using 3,5-diaminochlorobenzene as a starting material and reacting ammonia with 3,5-diaminochlorobenzene at a molar ratio of ammonia of 2 to 10 to 3,5-diaminochlorobenzene at a temperature of 150° to 250° C. in the presence of a copper compound catalyst.

DETAILED DESCRIPTION OF THE PREFERRED EMBODIMENTS

The present invention has been attained by the following findings.

(1) In a partial amination of sym-trihalogenobenzene, (i) a dechlorination is caused in the case of the use of 1,3,5 -trichlorobenzene and (ii) an ammonia water having high concentration such as at least 35% should be used in the case of the use of 1-bromo-3,5-dichlorobenzene.

(2) The reactivity of 3,5-diaminochlorobenzene in an amination is considered to be inferior to sym-trihalogenobenzene because of high electron density on benzene nuclear. Moreover, 3,5-diaminochlorobenzene is decomposed at about 120° C.

(3) It has been considered that 3,5-diaminochlorobenzene is decomposed, if it is used in an amination, so that the reaction will not perform or the reaction condition should be highly severe in comparison with the partial amination of sym-trihalogenobenzene.

(4) In the practical amination of 3,5-diaminochlorobenzene, however, the reaction is smoothly performed under a mild condition in comparison with the partial amination of sym-trihalogenobenzene. For example, the reaction can be performed with a smaller amount of ammonia water, in a lower concentration, at a lower temperature.

3,5-Diaminochlorobenzene used as the starting material in the process of the present invention is economically easily available under the recent industrial development of technology.

The copper compound catalysts used in the process of the present invention can be copper salts, oxides and hydroxides such as copper halides, oxides, hydroxides, and sulfates. Suitable copper compound catalysts include cuprous compounds such as cuprous chloride, cuprous bromide, cuprous iodide and cuprous oxide; and cupric compounds such as cupric sulfate, cupric oxide, cupric chloride and cupric hydroxide.

In the process of the present invention, a mixture of 3,5-diaminochlorobenzene, a copper compound catalyst and ammonia is heated to react them at a temperature of 150° to 250° C. In the reaction, ammonia water having a low concentration such as 10% or a high concentration of at least 35% can be used. It is also possible to feed ammonia gas into the mixture containing water to form a desired ammonia water. It is also possible to use liquid ammonia. A concentration of ammonia is usually at least 10% preferably in a range of 20 to 30%.

The copper compound catalyst is used at a ratio of 2 to 30 mol % preferably 5 to 10 mol % based on 3,5-diaminochlorobenzene. Ammonia is used at a molar ratio of 2 to 10 preferably 3 to 6 as $NH_3$ to 3,5-diaminochlorobenzene. It is preferable to use a desired amount of ammonia water having a concentration of 20 to 30% as $NH_3$ in an industrial process since the reaction is smoothly performed.

The reaction in the process of the present invention is usually carried out at a temperature of 150° to 250° C. preferably 160° to 190° C. The decomposition point of 3,5-diaminochlorobenzene as the starting material is about 120° C., Nevertheless, the reaction is smoothly performed at higher than 150° C. with less formation of decomposed products and by-products such as dechlorination products, deamination products, polymers and tar.

The reaction is usually carried out in an autoclave and the pressure of ammonia reached to 30 atm. or higher by heating. When the reaction temperature is lower than 150° C., the desired reaction is not performed whereas when it is higher than 250° C., large amounts of by-products and tar are produced. It is not advantages in an industrial process. The reaction is usually completed for 2 to 20 hours. 1,3,5-Triaminobenzene as the object product is obtained by a conventional purification of the reaction product at an yield of 50% or more. When 3,5-diaminochlorobenzene as the unreacted material is recovered, the compound can be reused.

1,3,5-Triaminobenzene obtained by the process of the present invention can be hydrolyzed by adding an aqueous solution of hydrochloric acid and heating the mixture to produce phloroglucine which is important as an industrial reagent.

The present invention will be further illustrated by certain examples and references which are provided for purposes of illustration only and are not intended to be limiting the present invention.

EXAMPLE 1

In an autoclave, 3.3 g. of 3,5-diaminochlorobenzene, 0.2 g. of cuprous chloride and 10 g. of liquid ammonia were charged to react them at 170° to 175° C. for 5 hours. After the reaction, the unreacted ammonia was discharged and a greyish black crystal was obtained. The product was purified by a silica gel column chromatography to obtain 1.7 g. of 1,3,5-triaminobenzene.

EXAMPLE 2

In accordance with the process of Example 1 except reacting them at 160° C. for 6 hours, the reaction was carried out and the product was purified to obtain 0.6 g. of 1,3,5-triaminobenzene and to recover about 2.0 g. of the unreacted 3,5-diaminochlorobenzene.

EXAMPLE 3

In an autoclave, 3.3 g. of 3,5-diaminochlorobbenzene, 0.3 g. of cupric chloride and 20 g. of 50% ammonia water were charged to react them at 170° C. for 16 hours to produce 1,3,5-triaminobenzene. After the reaction, nitrogen gas was fed to discharge ammonia gas and hydrochloric acid was added to neutralize the reaction mixture and 6 ml. of hydrochloric acid was further added and water was added to give a total volume of 50 ml. The mixture was refluxed in nitrogen gas flow to hydrolyze the product for 20 hours. The reaction mixture was cooled and the reaction product was extracted with ether, and dried and the solvent was distilled off to obtain 1.5 g. of phloroglucine.

EXAMPLE 4

In an autoclave, 3.3 g. of 3,5-diaminochlorobenzene, 20 g. of 50% ammonia water and 0.2 g. of cuprous oxide were charged to react them at 170° C. for 16 hours and the reaction product was purified by the process of Example 1 to obtain 0.9 g. of 1,3,5-triaminobenzene and to recover 0.9 g. of the unreacted 3,5-diaminochlorobenzene.

EXAMPLE 5

In an autoclave, 28.6 g. of 3,5-diaminochlorobenzene, 85 g. of 20% ammonia water and 1.0 g. of cuprous chloride were charged to react them at 175° to 180° C. for 8 hours to obtain 1,3,5-triaminobenzene. Ammonia was discharged and the product was recrystallized to obtain 20 g. of 1,3,5-triaminobenzene.

EXAMPLE 6

In an autoclave, 28.6 g. of 3,5-diaminochlorobenzene, 2 g. of cuprous chloride and 122 g. of 28% ammonia water were charged to react them at 165° to 170° C. for 8 hours to obtain 1,3,5-triaminobenzene. Ammonia was discharged and the product was recrystallized to obtain 19 g. of 1,3,5-triaminobenzene.

The reaction mixture was obtained by the same process and ammonia was discharged and hydrochloric acid was added to acidify the reaction mixture. The mixture was refluxed in nitrogen gas flow for 20 hours to hydrolyze the product. After the reaction, the reaction product was purified and recrystallized to obtain 17 g. of phloroglucine.

We claim:

1. A process for producing an aminobenzene comprising reacting ammonia at substantially higher than atmospheric pressure with 3,5-diaminochlorobenzene to produce 1,3,5-triaminobenzene at a temperature of 150° to 250° C. at a molar ratio of ammonia to 3,5-diaminochlorobenzene of 2 to 10 in the presence of a copper compound catalyst selected from the group consisting of copper salt, copper oxide, and copper hydroxide.

2. The process according to claim 1 wherein said copper compound catalyst is copper halide, copper sulfate, copper oxide, or copper hydroxide.

3. The process according to claim 1 wherein said copper compound catalyst is cuprous chloride, cupric chloride, cupric sulfate, cuprous oxide, cupric oxide, cuprous hydroxide or cupric hydroxide.

4. The process according to claim 1 wherein an amount of said copper compound catalyst is in a range of 2 to 30 mol % based on 3,5-diaminochlorobenzene.

5. The process according to claim 1 wherein said reaction is carried out by using ammonia at a molar ratio of 3 to 6 to 3,5-diaminochlorobenzene.

6. The process according to claim 1 wherein said reaction is carried out by using ammonia water having a concentration of 20 to 30 percents by weight.

7. The process according to claim 1 wherein said reaction is carried out at a temperature of 160° to 190° C.

* * * * *

UNITED STATES PATENT AND TRADEMARK OFFICE
CERTIFICATE OF CORRECTION

PATENT NO. : 4,380,670

DATED : April 19, 1983

INVENTOR(S) : RYUZO NISHIYAMA ET AL

It is certified that error appears in the above-identified patent and that said Letters Patent is hereby corrected as shown below:

On the title page:
Please insert the following Foreign Application Priority Data--[30] Foreign Application Priority Data April 24, 1980 [JP] Japan...54700/1980--.

Signed and Sealed this

Twenty-sixth Day of July 1983.

[SEAL]

Attest:

GERALD J. MOSSINGHOFF

Attesting Officer

Commissioner of Patents and Trademarks